(12) United States Patent
Guntoori et al.

(10) Patent No.: US 7,193,090 B2
(45) Date of Patent: Mar. 20, 2007

(54) PREPARATION OF ATORVASTATIN

(75) Inventors: Bhaskar Reddy Guntoori, Brantford (CA); Daqing Che, Brantford (CA); Fan Wang, Hamilton (CA); Yajun Zhao, Brantford (CA); K. S. Keshava Murthy, Ancaster (CA); Stephen E. Horne, Burlington (CA)

(73) Assignee: Apotex Pharmachem Inc., Brantford (CA)

( * ) Notice: Subject to any disclaimer, the term of this patent is extended or adjusted under 35 U.S.C. 154(b) by 305 days.

(21) Appl. No.: 10/800,741

(22) Filed: Mar. 16, 2004

(65) Prior Publication Data
US 2005/0203302 A1 Sep. 15, 2005

(30) Foreign Application Priority Data
Mar. 15, 2004 (CA) .................... 2460935

(51) Int. Cl.
*C07D 207/00* (2006.01)
(52) U.S. Cl. ..................................... 548/537
(58) Field of Classification Search ................. 548/537
See application file for complete search history.

(56) References Cited

U.S. PATENT DOCUMENTS 5,273,995 A 12/1993 Roth .................... 514/422

OTHER PUBLICATIONS

Brooks, D.W., et al. "C-Acylation under Virtually Neutral Conditions", *Angew. Chem. Int. Ed. Engl.*, (1979) 18, No. 1, pp. 72-74.
Brower, P.L., et al., "The Synthesis of (4R-cis)-1,1-Dimethylethyl 6-cyanomethyl-2,2-dimethyl-1,3-dioxane-4-acetate, a Key Intermediate for the Preparation of Cl-981, a Highly Potent, Tissue Selective Inhibitor of HMG-CoA Reductase", *Tetrahedron Letters*, (1992) vol. 33, No. 17, pp. 2279-2282.

*Primary Examiner*—Joseph K. McKane
*Assistant Examiner*—Robert Shiao
(74) *Attorney, Agent, or Firm*—Marcelo K. Sarkis; Ivor M. Hughes; Neil H. Hughes

(57) ABSTRACT

A process for preparing (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid, tert-butylester comprising:

(a) reduction of 5-[2-(4-fluorophenyl)-5-(1-methylethyl)-3-phenyl-4-[(phenylamino)carbonyl]-1H-pyrrol-1-yl]-3-oxo-1-pentanoic acid, (R)-2-hydroxy-1,2,2-triphenylethyl ester;

(b) hydrolysis of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (R)-2-hydroxy-1,2,2-triphenylethyl ester using an alkali base in a solvent to form the acid;

(c) alkylation of the acid forming (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid, tert-butylester.

15 Claims, No Drawings

PREPARATION OF ATORVASTATIN

FIELD OF THE INVENTION

The present invention relates to an improved process for preparing Atorvastatin and pharmaceutically acceptable salts thereof.

BACKGROUND OF THE INVENTION

Atorvastatin is a reductase inhibitor of the enzyme 3-hydroxy-3-methylglutarate-coenzyme A (HMG-CoA) and therefore is a useful anti-hyperlipoproteinemic agent. It has proven to be a highly effective medicament for the treatment of disorders such as hyperlipidemia and hypercholesterolemia which are conditions that are known risk factors for arteriosclerosis and coronary heart disease. Atorvastatin is chemically [R-(R*,R*)]-2-(4-fluorophenyl)-β,δ-dihydroxy-5-(1-methylethyl)-3-phenyl-4-(phenylcarbamoyl)-1H-pyrrole-1-heptanoic acid and is marketed as its calcium salt under the brand name Lipitor™.

A route to Atorvastatin (6) is taught in U.S. Pat. No. 5,273,995. Depicted in Scheme 1 herein is a sequence of reactions from the process taught in U.S. Pat. No. 5,273,995 involving the alkylation of aldehyde 1 to form the chiral ester 2 followed by transesterification to the methylester 3 using sodium methoxide. Methylester 3 is then reacted with the lithium enolate of tert-butylacetate to form the β-ketoester 5, which is then further reacted over a series of steps to form Atorvastatin Calcium (6). If scale-up of this transformation (2 to 5) were contemplated, then this route would suffer from serious deficiencies. These include:

a. purification of the β-hydroxy methylester 2 via silica gel column purification
b. no mention is made regarding the recovery of the expensive chiral auxiliary [(S)-1,1,2-triphenyl-1,2-ethanediol, 4]
c. the initial transesterification step employs the expensive, flammable and corrosive base sodium methoxide under anhydrous conditions
d. sodium methoxide is also a strong base which may lead to side reactions
e. the formation of the enolate of tert-butylacetate used in the formation of 5 is accomplished using lithium diisopropylamine which requires a separate preparative step and the use of diisopropylamine and n-butyllithium in THF at −40° C.
f. the reaction temperature required for the subsequent alkylation of the α-hydroxy methylester 3 with the lithium enolate of tert-butylacetate is very low (−70° C.)
g. example 3 of U.S. Pat. No. 5,273,995 requires the addition of the α-hydroxy methylester 3 in absolute THF to the lithium enolate solution "as quickly as possible without allowing the temperature to rise above −40° C.".

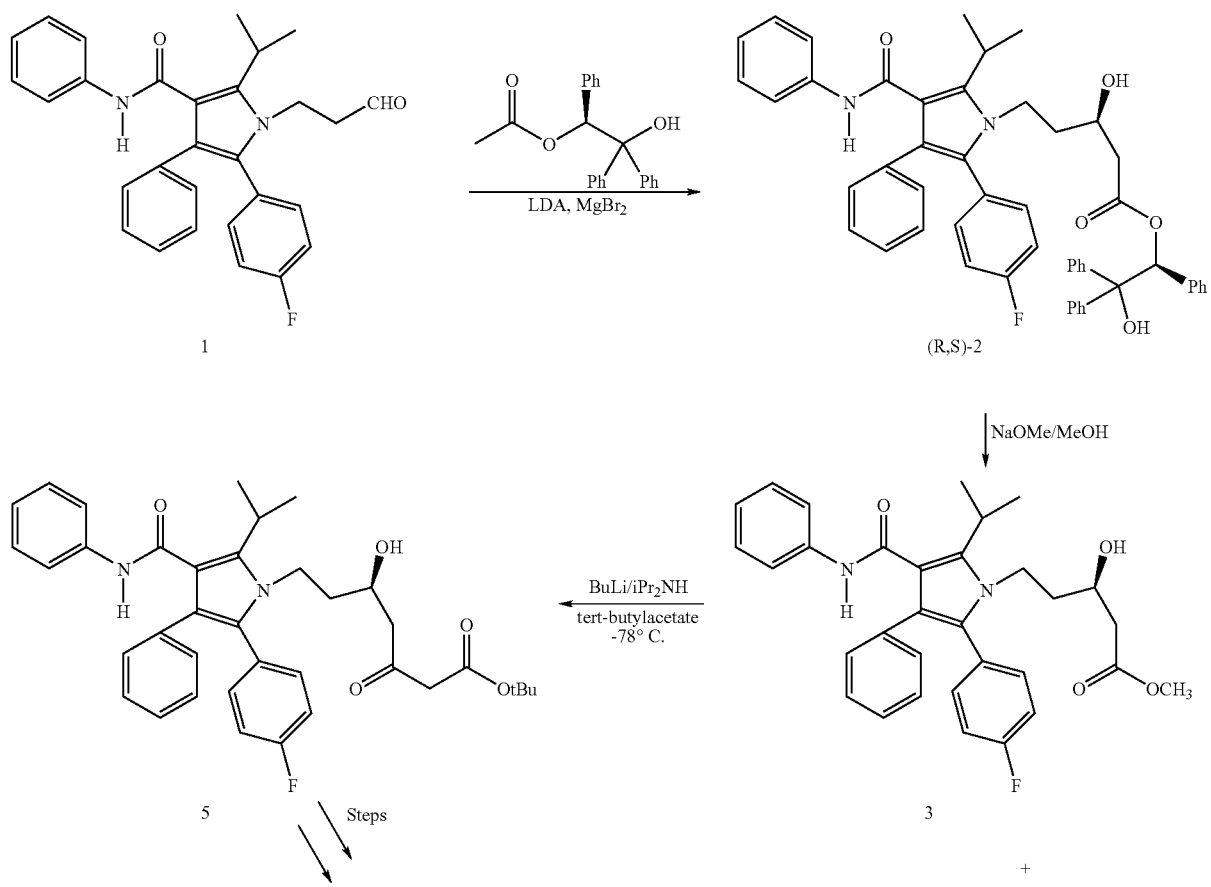

Scheme 1

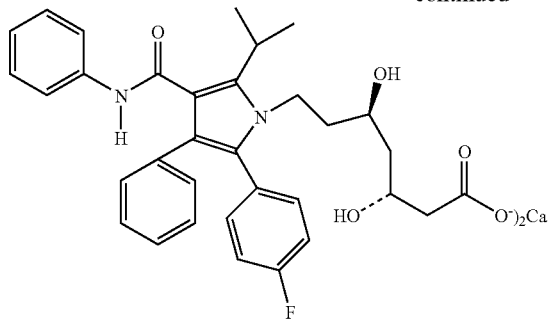

Thus, work was undertaken to overcome the deficiencies of the prior art and to provide a facile and commercially viable process, and to provide a method that would allow convenient recovery of the expensive chiral auxiliary 4 [(S)-1,1,2-triphenyl-1,2-ethanediol] in enantiomerically pure form. This permits re-use in the process after acetylation of the secondary hydroxyl group.

SUMMARY OF THE INVENTION

It has been unexpectedly and surprisingly discovered that this transformation can be accomplished using a straightforward, robust and scalable method that employs cost-effective and safe reagents throughout. This novel route is depicted in Scheme 2 below.

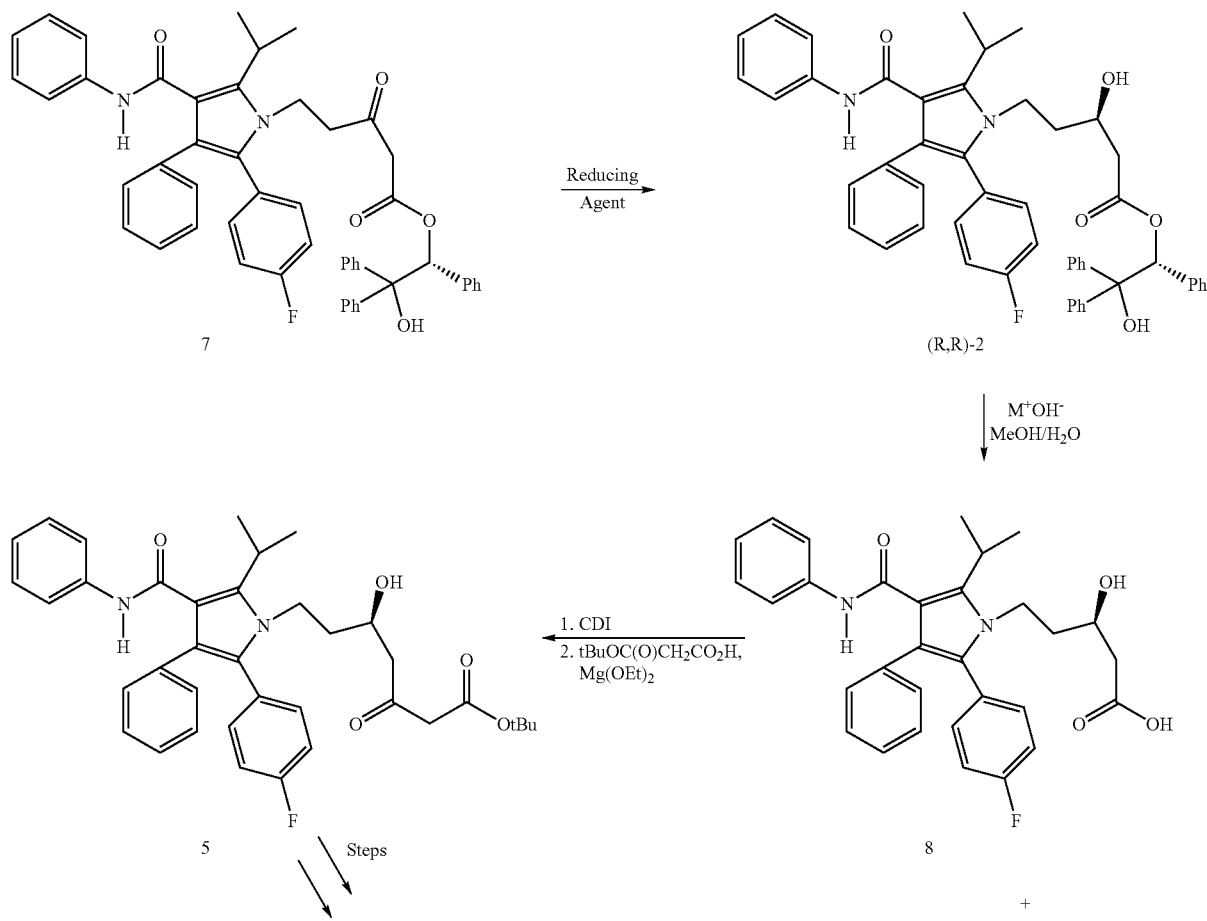

-continued

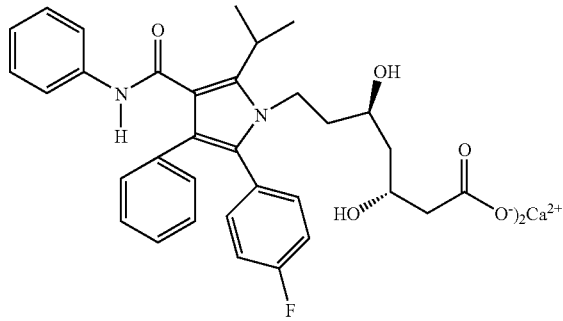

6, Atorvastatin Calcium

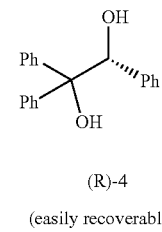

(R)-4
(easily recoverable)

There are numerous advantages of this route beginning from the chiral β-ketoester 7. The desired chirality of 2 is achieved by using the chirality on the auxiliary to predominantly induce the requisite R chirality at the hydroxyl stereocentre. Other advantages include the hydrolysis reaction from 7 to 2 may be carried out with an alkali base, preferably with an alkali metal hydroxide base, preferably in an aqueous media at from about 15° C. to about 65° C., conditions which are more amenable to scale-up. Also, relative to sodium methoxide, alkali metal hydroxides are inexpensive and non-flammable and are weaker bases thereby minimizing potential side-reactions.

Examples of alkali metal hydroxide bases that are suitable for the hydrolysis reaction include lithium hydroxide, sodium hydroxide and potassium hydroxide. Particularly suitable bases are sodium hydroxide or potassium hydroxide. An even more particularly suitable base is potassium hydroxide. The hydrolysis reaction may be carried out using from about 1 to about 10 equivalents of the alkali metal hydroxide, more preferably from about 2 to about 8 equivalents, and most preferably about 5 equivalents. Preferably, the hydrolysis reaction is accomplished in a solvent, preferably methanol or water or mixtures thereof.

This hydrolysis reaction forms the β-hydroxy carboxylic acid 8 intermediate that is easily isolable and stable. The chemical name we have assigned this novel β-hydroxy carboxylic acid 8 is (R)-5-[2-(4-fluorophenyl)-5-(1-methylethyl)-3-phenyl-4-[(phenylamino)carbonyl]-1H-pyrrol-1-yl]-3-hydroxy-1-pentanoic acid. Furthermore, when 8 is isolated by this process, it may be used without purification for further elaboration to 5 and eventually Atorvastatin 6 and its calcium salt, or other salts. The conversion of 5 to 6 may be done based on procedures known in the art. This novel β-hydroxy carboxylic acid 8 also has good handling properties and is easily dried.

Another aspect of this invention which represents a highly advantageous feature of this process is that the chiral auxiliary (R)-4 [(R)-1,1,2-triphenyl-1,2-ethanediol] can also be conveniently isolated by filtration and then recycled, thereby minimizing the overall cost and reducing waste throughout the process.

Another aspect of this invention is that, if desired, the β-hydroxy carboxylic acid 8 intermediate can be converted to the methylester 3 using standard esterification methods known in the art.

In another aspect of this invention, if desired, one can directly convert 2 into 5 without isolation of the intermediate β-hydroxy carboxylic acid 8. This variation has further advantages including cost-effectiveness. For instance, the conversion of 2 into 5 without isolation of 8 removes the necessity, if needed, of drying 8, thereby reducing the overall cycle time.

In another aspect of the invention, the further elaboration to the β-ketoester 5 is accomplished by activation of the acid 8 using a carboxylic acid activating agent such as 1,1'-carbonyldiimidazole (CDI) and the like followed by addition of mono-tert-butyl malonate in the presence of a base, such as magnesium ethoxide or the like, preferably under mild (room temperature) conditions. This process is more easily scaled to commercial quantities relative to the one taught in U.S. Pat. No. 5,273,995.

According to one aspect of the invention, there is provided a process for preparing (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid, tert-butylester (5) comprising:
  (a) reduction of 5-[2-(4-fluorophenyl)-5-(1-methylethyl)-3-phenyl-4-[(phenylamino)carbonyl]-1H-pyrrol-1-yl]-3-oxo-1-pentanoic acid, (R)-2-hydroxy-1,2,2-triphenylethyl ester (7);
  (b) hydrolysis of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (R)-2-hydroxy-1,2,2-triphenylethyl ester (7) using an alkali base, preferably an alkali metal base as the alkali base, preferably selected from the group consisting of lithium hydroxide, sodium hydroxide or potassium hydroxide, preferably in a solvent to form the acid (8);
  (c) alkylation of the acid (8) forming (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid, tert-butylester (5).

Preferably the solvent used during hydrolysis is methanol or water or a mixture thereof.

Preferably the alkali metal base is in the amount from about 1 to about 10 equivalents, more preferably from about 2 to about 8 equivalents, even more preferably about 5 equivalents.

According to yet another aspect of the invention, there is provided (R)-5-[2-(4-fluorophenyl)-5-(1-methylethyl)-3-phenyl-4-[(phenylamino)carbonyl]-1H-pyrrol-1-yl]-3-hydroxy-1-pentanoic acid (8).

According to yet another aspect of the invention, there is provided a process for the preparation of Atorvastatin or pharmaceutically acceptable salts thereof using the processes described herein.

Preferably when using the processes described herein the (R)-1,1,2-triphenyl-1,2-ethanediol (R)-4 is recovered.

More preferably the (R)-1,1,2-triphenyl-1,2-ethanediol (R)-4 is recovered in optically enriched form.

According to one embodiment, the intermediate (R)-5-[2-(4-fluorophenyl)-5-(1-methylethyl)-3-phenyl-4-[(phenylamino)carbonyl]-1H-pyrrol-1-yl]-3-hydroxy-1-pentanoic acid (8) is not isolated during the process.

According to yet another embodiment, the (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid tert-butylester (5) is prepared using mono-tert-butyl malonate in the presence of a base, preferably said base is a metal alkoxide, even more preferably said base is magnesium ethoxide.

According to yet another embodiment of the invention, there is provided a process for the preparation of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, methylester (3) from (R)-5-[2-(4-fluorophenyl)-5-(1-methylethyl)-3-phenyl-4-[(phenylamino)carbonyl]-1H-pyrrol-1-yl]-3-hydroxy-1-pentanoic acid.

According to yet another embodiment, there is provided a process for the preparation of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid comprising hydrolysis of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (R)-2-hydroxy-1,2,2-triphenylethyl ester, wherein the said hydrolysis is carried out using a base, preferably said process is carried out in the presence of a solvent.

According to yet another embodiment, there is provided a process for the preparation of the novel 5-[2-(4-fluorophenyl)-5-(1-methylethyl)-3-phenyl-4-[(phenylamino)carbonyl]-1H-pyrrol-1-yl]-3-oxo-1-pentanoic acid, (R)-2-hydroxy-1,2,2-triphenylethyl ester (7). In one instance, (7) is accessible by the oxidation of 5-[2-(4-fluorophenyl)-5-(1-methylethyl)-3-phenyl-4-[(phenylamino)carbonyl]-1H-pyrrol-1-yl]-3-hydroxy-1-pentanoic acid, (R)-2-hydroxy-1,2,2-triphenylethyl ester, as described in Example 6.

EXAMPLES

Example 1

Preparation of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (R)-2-hydroxy-1,2,2-triphenylethyl ester (2)

A solution of 5-[2-(4-fluorophenyl)-5-(1-methylethyl)-3-phenyl-4-[(phenylamino)carbonyl]-1H-pyrrol-1-yl]-3-oxo-1-pentanoic acid, (R)-2-hydroxy-1,2,2-triphenylethyl ester (0.1 g, 0.127 mmol., 7) in 6 ml of THF/MeOH (1:2, v/v) was cooled to −78° C. To this solution was added sodium borohydride (20 mg) in two portions over a period of 0.5 h. The resulting reaction mixture was stirred at −78° C. for an additional 1 hour under nitrogen and then quenched with aqueous saturated $NH_4Cl$ solution and extracted with dichloromethane (10 mL×2). The combined dichloromethane layers were washed with brine (5 mL×2), dried ($Na_2SO_4$) and evaporated to give a white crystalline solid (0.94 g, 94%).

$^1$H-NMR and HPLC analysis shows a mixture of two diastereomers in ratio 3:1(3R/3S).

$^1$H-NMR (300 MHz, $CDCl_3$) (for the major diastereomer, 3R): δ(ppm)=1.51(d, 6H, J=7.0 Hz), 1.57(m, 2H), 2.22(m, 2H), 2.59(d, 1H, J=4.1 Hz), 2.80(s, 1H), 3.50–3.58(m, 1H), 3.61–3.73(m, 1H), 3.80–3.92(m, 1H), 4.0–4.14(m, 1H), 6.69 (s, 1H), 6.85(s, 1H), 6.93–7.57(m, 28H); (for the minor diastereomer, 3S): δ(ppm)=1.51(d, 6H, J=7.0 Hz), 1.57(m, 2H), 2.22(m, 2H), 2.46(d, 1H, J=3.8 Hz), 2.78(s, 1H), 3.50–3.58(m, 1H)3.61–3.73(m, 1H), 3.80–3.92(m, 1H), 4.0–4.14(m, 1H), 6.69(s, 1H), 6.85(s, 1H), 6.93–7.57(m, 29H).

Example 2

Preparation of (R)-5-[2-(4-Fluorophenyl)-5-(1-methylethyl)-3-phenyl-4-[(phenylamino)carbonyl]-1H-pyrrol-1-yl]-3-hydroxy-1-pentanoic acid (8)

To a suspension of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (S)-2-hydroxy-1,2,2-triphenylethyl ester (7.9 g, 10 mmol.) in 144 mL of MeOH/$H_2O$ (3.5:1, v/v) was added potassium hydroxide (5.5 g, 100 mmol.). After refluxing for 4 hours, the mixture was cooled to room temperature whereupon 48 mL of water was added and the mixture was stirred a further 1-2 hours. The recovered (S)-1,1,2-triphenylethanediol was collected by filtration and washed with 30 mL of MeOH/$H_2O$ (1:3, v/v). The solid was dried under reduced pressure at 45–50° C. (2.7 g, 92%). The filtrate was evaporated to remove methanol and the pH was adjusted to 2–2.5 using a 1 M HCl solution. The resulting suspension was stirred at room temperature for 1–2 hours. The product was collected by Buchner filtration and the filter cake was washed with 30 mL of water and dried at 45–50° C. (4.7 g, 91%).

$^1$H-NMR (300 MHz, $CDCl_3$): δ/ppm=1.52(d,6H,J=6.8 Hz), 1.63–1.80(m,2H),2.34 (d,2H, J=5.5 Hz), 3.50–3.58(m, 1H), 3.75–3.90(m,1H), 3.90–4.0(m,1H), 4.10–4.20(m,1H), 6.89(s,1H), 6.96–7.39(m,14H).

HRMS: m/z 514.2267 amu (514.2268 calculated for $C_{31}H_{31}FN_2O_4$).

Similarly, (R)-5-[2-(4-fluorophenyl)-5-(1-methylethyl)-3-phenyl-4-[(phenylamino)carbonyl]-1H-pyrrol-1-yl]-3-hydroxy-1-pentanoic acid (8) can be prepared from (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (R)-2-hydroxy-1,2,2-triphenylethyl ester.

Example 3

Preparation of (R)-5-[2-(4-Fluorophenyl)-5-(1-methylethyl)-3-phenyl-4-[(phenylamino)carbonyl]-1H-pyrrol-1-yl]-5-hydroxy-3-oxo-1-heptanoic acid, tert-butylester (5) from the acid (8)

1,1'-Carbonyldiimidazole (0.37 g) was added to a solution of the acid (8) (1.0 g) obtained from Example 2 in 10 mL THF. After stirring at room temperature for 3 hours, the magnesium salt prepared from reaction of magnesium ethoxide (0.58 g) and mono-tert-butyl malonate (1.7 g) was added. The mixture was stirred for 20 hours at room temperature and then the solvent was removed at reduced pressure. The residue was partitioned between ethyl acetate and aqueous 1 M HCl and the layers were separated. The aqueous phase was further extracted with ethyl acetate. The combined organic phases were washed with aqueous saturated $NaHCO_3$ and brine. After drying and purifying, the β-ketoester 5 (0.5 g) was produced. The analytical data are consistent with the assigned structure.

9

Example 4

Preparation of (R)-5-[2-(4-Fluorophenyl)-5-(1-methylethyl)-3-phenyl-4-[(phenylamino)carbonyl]-1H-pyrrol-1-yl]-3-hydroxy-1-pentanoic acid, methylester (3) from the acid (8)

To a suspension of the acid (8) (1.1 g) obtained from Example 2 in 5.5 mL methanol with 1 drop of DMF at 0° C. was added dropwise thionyl chloride (0.4 g). The mixture was stirred at room temperature for 2 hours and then the solvent was removed at reduced pressure. The residue was dissolved in ethyl acetate and washed with aqueous saturated $NaHCO_3$, water and brine. After drying and evaporating, the methylester 3 (1.02 g) was produced. The analytical data are consistent with the assigned structure.

Example 5

Preparation of (R)-5-[2-(4-Fluorophenyl)-5-(1-methylethyl)-3-phenyl-4-[(phenylamino)carbonyl]-1H-pyrrol-1-yl]-5-hydroxy-3-oxo-1-heptanoic acid, tert-butylester (5) from (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (S)-2-hydroxy-1,2,2-triphenylethyl ester (2)

To a suspension of (R)-5-[2-(4-fluorophenyl)-5-(1-methylethyl)-3-phenyl-4-[(phenylamino)carbonyl]-1H-pyrrol-1-yl]-3-hydroxyl-1-pentanoic acid, (S)-2-hydroxy-1,2,2-triphenylethyl ester (2) (4.0 g) in 77 mL of $MeOH/H_2O$ (3.5:1, v/v) was added potassium hydroxide (2.8 g). After refluxing for 4 hours the mixture was cooled to room temperature followed by addition of 26 mL water and stirring for 1–2 hours. The recovered (S)-1,1,2-triphenylethanediol was collected by filtration and washed with 30 mL of $MeOH/H_2O$ (1:3, v/v). The solid was dried under reduced pressure at 45–50° C. (1.3 g). The filtrate was evaporated to remove methanol and then 50 mL ethyl acetate was added. The mixture was adjusted to pH 2–2.5 with 1 M HCl solution and the layers were separated. The aqueous phase was further extracted with ethyl acetate. The combined organic phase was washed with brine, dried over anhydrous $Na_2SO_4$, filtered and evaporated. The residue was dissolved in 20 mL THF followed by addition of 1,1'-carbonyldiimmidazole (0.91 g). After stirring for 3 hours at room temperature, the magnesium salt prepared from reaction of magnesium ethoxide (0.86 g) and mono-tert-butyl malonate (2.5 g) in THF was added. The mixture was stirred for 20 hours at room temperature and then the solvent was removed at reduced pressure. The residue was partitioned between ethyl acetate and aqueous 1 M HCl and the layers were separated. The aqueous phase was further extracted with ethyl acetate. The combined organic phases were washed with aqueous saturated $NaHCO_3$ and brine. After drying and purifying, the β-ketoester 5 (0.48 g) was produced. The analytical data are consistent with the assigned structure.

$^1$H-NMR (300 MHz, $CDCl_3$): δ/ppm=1.45(s,9H), 1.53 (dd,6H,$J_1$=1.8 Hz,$J_2$=1.80(m,2H), 2.50(s,1H), 2.53(d,1H, J=1.9 Hz), 3.30(s,2H), 3.49–3.61(m,1H), 3.87–4.00(m,2H), 4.08–4.20(m,1H), 6.85(s,1H), 6.95–7.10(m,5H), 7.10–7.22 (m,9H).

10

Example 6

Preparation of 5-[2-(4-fluorophenyl)-5-(1-methylethyl)-3-phenyl-4-[(phenylamino)carbonyl]-1H-pyrrol-1-yl]-3-oxo-1-pentanoic acid, (R)-2-hydroxy-1,2,2-triphenylethyl ester (7) from (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (R)-2-hydroxy-1,2,2-triphenylethyl ester (2)

To a solution of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (R)-2-hydroxy-1,2,2-triphenylethyl ester (6.0 g, 7.62 mmol) in dichloromethane (120 ml) was added sodium bicarbonate (2.6 g). The mixture was cooled to 0° C. and then Dess-Martin periodinone (4.3 g, 1,1,1-tris(acetyloxy)-1,1-dihydro-1,2-benziodoxol-3-(1H)-one) was added in portions. The resulting reaction mixture was stirred at 0° C. for additional 4 hours under nitrogen before quenching with water. The two layers were separated and the aqueous layer was extracted with dichloromethane. The combined organic layers were washed with brine and dried with sodium sulfate and the product was purified by column chromatography to give 4.8 g of 2 as a white solid.

$^1$H-NMR(300 MHz, $CDCl_3$): δ(ppm)=1.50(m, 6H), 2.31–2.70(m, 3H), 3.2(s, 2H), 3.40–3.55(m, 1H), 4.10–4.21 (m, 1H), 6.69(s, 1H), 6.87(s, 1H), 6.96–7.58(m, 29H)

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A process for preparing (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid, tert-butylester comprising:
    (a) reduction of 5-[2-(4-fluorophenyl)-5-(1-methylethyl)-3-phenyl-4-[(phenylamino)carbonyl]-1H-pyrrol-1-yl]-3-oxo-1-pentanoic acid, (R)-2-hydroxy-1,2,2-triphenylethyl ester;
    (b) hydrolysis of (R)-5-[2-(4-fluorophenyl)-5-(1-methylethyl)-3-phenyl-4-[(phenylamino)carbonyl]-1H-pyrrol-1-yl]-3-hydroxy-1-pentanoic acid, (R)-2-hydroxy-1,2,2-triphenylethyl ester using an alkali base in a solvent to form the acid;
    (c) alkylation of the acid forming (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid, tert-butylester.

2. A process for the preparation of (R)-5-[2-(4-fluorophenyl)-5-(1-methylethyl)-3-phenyl-4-[(phenylamino)carbonyl]-1H-pyrrol-1-yl]-5-hydroxy-3-oxo -1-heptanoic acid, tert-butylester according to claim 1 using an alkali metal hydroxide as the alkali base.

3. A process for the preparation of (R)-5-[2-(4-fluorophenyl)-5-(1-methylethyl)-3-phenyl-4-[(phenylamino)carbonyl]-1H-pyrrol-1-yl]-5-hydroxy-3-oxo -1-heptanoic acid, tert-butylester according to claim 1 using lithium hydroxide, sodium hydroxide or potassium hydroxide.

4. A process for the preparation of (R)-5-[2-(4-fluorophenyl)-5-(1-methylethyl)-3-phenyl-4-[(phenylamino)carbonyl]-1H-pyrrol-1-yl]-5-hydroxy-3-oxo -1-heptanoic acid, tert-butylester according to claim 1 using sodium hydroxide.

5. A process for the preparation of (R)-5-[2-(4-fluorophenyl)-5-(1-methylethyl)-3-phenyl-4-[(phenylamino)carbonyl]-1H-pyrrol-1-yl]-5-hydroxy-3-oxo -1-heptanoic acid, tert-butylester according to claim 1 using potassium hydroxide.

6. A process for the preparation of (R)-5-[2-(4-fluorophenyl)-5-(1-methylethyl)-3-phenyl-4-[(phenylamino)carbonyl]-1H-pyrrol-1-yl]-5-hydroxy-3-oxo -1-heptanoic acid, tert-butylester according to claim 1 where the solvent is methanol or water or a mixture thereof.

7. A process for the preparation of (R)-5-[2-(4-fluorophenyl)-5-(1-methylethyl)-3-phenyl-4-[(phenylamino)carbonyl]-1H-pyrrol-1-yl]-5-hydroXy-3-oxo -1-heptanoic acid, tert-butylester according to claim 1 using from about 1 to about 10 equivalents of an alkali metal base.

8. A process for the preparation of (R)-5-[2-(4-fluorophenyl)-5-(1-methylethyl)-3-phenyl-4-[(phenylamino)carbonyl]-1H-pyrrol-1-yl]-5-hydroXy-3-oxo -1-heptanoic acid, tert-butylester according to claim 1 using from about 2 to about 8 equivalents of an alkali metal base.

9. A process for the preparation of (R)-5-[2-(4-fluorophenyl)-5-(1-methylethyl)-3-phenyl-4-[(phenylamino)carbonyl]-1H-pyrrol-1-yl]-5-hydroxy-3-oxo -1-heptanoic acid, tert-butylester according to claim 1 using about 5 equivalents of an alkali metal base.

10. A process according to any one of claims 1, 2, 3, 4, 5, 6, 7, 8, or 9 where the chiral auxiliary (R)-1,1,2-triphenyl-1,2-ethanediol is recovered.

11. A process according to claim 10 where the chiral auxiliary (R) -1,1,2-triphenyl-1,2-ethanediol is recovered in optically enriched form.

12. A process according to any one of claims 1, 2, 3, 4, 5, 6, 7, 8, or 9 where the intermediate (R)-5-[2-(4-fluorophenyl)-5-(1-methylethyl)-3-phenyl-4-[(phenylamino)carbonyl]-1H-pyrrol-1-yl]-3-hydroxy-1-pentanoic acid is not isolated.

13. A process according to any one of claims 1, 2, 3, 4, 5, 6, 7, 8, or 9 where (R)-5-[2-(4-fluorophenyl)-5-(1-methylethyl)-3-phenyl-4-[(phenylamino)carbonyl]-1H-pyrrol-1-yl]-5-hydroxy-3-oxo-1-heptanoic acid tert-butylester is prepared using mono-tert-butyl malonate in the presence of a base.

14. A process according to claim 13 where the base is a metal alkoxide.

15. A process according to claim 14 where the base is magnesium ethoxide.

* * * * *